(12) United States Patent
Hufnagel et al.

(10) Patent No.: US 9,936,951 B2
(45) Date of Patent: Apr. 10, 2018

(54) INTERCHANGEABLE TIP RELOAD

(71) Applicant: Covidien LP, Mansfield, MA (US)

(72) Inventors: Elizabeth Hufnagel, Boulder, CO (US);
Gregg Krehel, Newtown, CT (US);
Jason Iceman, Chesire, CT (US); **Erik
Carlson, Newington, CT (US); Ramiro
Cabrera, Chesire, CT (US); Kenneth
Whitfield**, North Haven, CT (US)

(73) Assignee: Covidien LP, Mansfield, MA (US)

( * ) Notice: Subject to any disclaimer, the term of this patent is extended or adjusted under 35 U.S.C. 154(b) by 740 days.

(21) Appl. No.: 14/147,683

(22) Filed: Jan. 6, 2014

(65) Prior Publication Data

US 2014/0263555 A1    Sep. 18, 2014

Related U.S. Application Data

(60) Provisional application No. 61/777,269, filed on Mar. 12, 2013.

(51) Int. Cl.
*A61B 17/068* (2006.01)
*A61B 17/00* (2006.01)
(Continued)

(52) U.S. Cl.
CPC ...... *A61B 17/068* (2013.01); *A61B 17/00234* (2013.01); *A61B 17/07207* (2013.01); *A61B 17/07292* (2013.01); *A61B 2017/00473* (2013.01); *A61B 2017/0688* (2013.01); *A61B 2017/07214* (2013.01); *A61B 2017/07257* (2013.01); *A61B 2017/07271* (2013.01); *A61B 2017/2946* (2013.01); *A61B 2017/320044* (2013.01)

(58) Field of Classification Search
CPC . A61B 17/068; A61B 17/0686; A61B 17/072; A61B 17/115; A61B 17/1155; A61B 17/07207; A61B 17/07292; A61B 2017/07214; A61B 17/00234; A61B 2017/00473; A61B 2017/32044
USPC .............. 227/19, 175.1, 176.1, 178.1, 180.1; 606/139, 153, 219, 190
See application file for complete search history.

(56) References Cited

U.S. PATENT DOCUMENTS 2,887,111 A    5/1959   Diaz
4,545,373 A    10/1985  Christoudias
(Continued)

FOREIGN PATENT DOCUMENTS

CN    101234032 A    8/2008
EP    1 943 976      7/2008
(Continued)

OTHER PUBLICATIONS

European Search Report dated Jul. 1, 2014 issued in EP 14 15 8732.
(Continued)

*Primary Examiner* — Scott A. Smith

(57) ABSTRACT

A surgical device including an end effector that is configured and adapted to receive an interchangeable tip is disclosed. Also disclosed are several interchangeable tips that are configured and adapted for different surgical procedures. The interchangeable tips facilitate the performance of different surgical procedures while using the same device.

2 Claims, 6 Drawing Sheets

(51) Int. Cl.
  *A61B 17/072* (2006.01)
  *A61B 17/32* (2006.01)
  *A61B 17/29* (2006.01)

(56) References Cited

U.S. PATENT DOCUMENTS

| | | | |
|---|---|---|---|
| 4,576,164 A | 3/1986 | Richeson | |
| 4,601,710 A | 7/1986 | Moll | |
| 4,723,545 A | 2/1988 | Nixon et al. | |
| 4,873,977 A | 10/1989 | Avant et al. | |
| 5,047,039 A | 9/1991 | Avant et al. | |
| 5,129,570 A | 7/1992 | Schulze et al. | |
| 5,217,460 A | 6/1993 | Knoepfler | |
| 5,234,454 A | 8/1993 | Bangs | |
| 5,281,236 A | 1/1994 | Bagpato et al. | |
| 5,282,807 A | 2/1994 | Knoepfler | |
| 5,350,104 A | 9/1994 | Main et al. | |
| 5,355,897 A | 10/1994 | Pietrafitta et al. | |
| 5,360,154 A | 11/1994 | Green | |
| 5,376,376 A | 12/1994 | Li | |
| 5,383,880 A * | 1/1995 | Hooven | A61B 17/07207 227/175.1 |
| 5,389,098 A * | 2/1995 | Tsuruta | A61B 17/00234 606/142 |
| 5,395,033 A * | 3/1995 | Byrne | A61B 17/07207 227/175.1 |
| 5,397,324 A | 3/1995 | Carroll et al. | |
| 5,425,745 A | 6/1995 | Green et al. | |
| 5,445,644 A | 8/1995 | Pietrafitta et al. | |
| 5,467,911 A | 11/1995 | Tsuruta et al. | |
| 5,487,500 A | 1/1996 | Knodel et al. | |
| 5,501,654 A | 3/1996 | Failla et al. | |
| 5,507,754 A | 4/1996 | Green et al. | |
| 5,522,788 A | 6/1996 | Kuzmak | |
| 5,527,298 A | 6/1996 | Vance et al. | |
| 5,531,744 A | 7/1996 | Nardella et al. | |
| 5,562,241 A | 10/1996 | Knodel et al. | |
| 5,597,107 A | 1/1997 | Knodel et al. | |
| 5,603,698 A | 2/1997 | Roberts et al. | |
| 5,632,432 A | 5/1997 | Schulze et al. | |
| 5,662,258 A | 9/1997 | Knodel et al. | |
| 5,665,100 A | 9/1997 | Yoon | |
| 5,690,653 A | 11/1997 | Richardson et al. | |
| 5,766,187 A | 6/1998 | Sugarbaker | |
| 5,772,099 A | 6/1998 | Gravener | |
| 5,782,397 A * | 7/1998 | Koukline | A61B 17/0686 227/119 |
| 5,810,855 A | 9/1998 | Rayburn et al. | |
| 5,816,471 A | 10/1998 | Plyley et al. | |
| 5,902,333 A | 5/1999 | Roberts et al. | |
| 5,908,427 A | 6/1999 | McKean et al. | |
| 5,984,964 A | 11/1999 | Roberts et al. | |
| 6,003,517 A | 12/1999 | Sheffield et al. | |
| 6,032,849 A | 3/2000 | Mastri et al. | |
| 6,099,537 A | 8/2000 | Sugai et al. | |
| 6,099,551 A | 8/2000 | Gabbay | |
| 6,117,148 A | 9/2000 | Ravo et al. | |
| 6,149,660 A | 11/2000 | Laufer et al. | |
| 6,165,183 A | 12/2000 | Kuehn et al. | |
| 6,193,129 B1 | 2/2001 | Bittner et al. | |
| 6,221,083 B1 * | 4/2001 | Mayer | A61B 17/062 606/139 |
| 6,264,086 B1 * | 7/2001 | McGuckin, Jr. | A61B 17/00234 227/175.1 |
| 6,443,970 B1 | 9/2002 | Schulze et al. | |
| 6,458,128 B1 | 10/2002 | Schulze | |
| 6,464,702 B2 | 10/2002 | Schulze et al. | |
| 6,506,210 B1 | 1/2003 | Kanner | |
| 6,530,942 B2 | 3/2003 | Fogarty et al. | |
| 6,554,829 B2 | 4/2003 | Schulze et al. | |
| 6,582,452 B2 | 6/2003 | Coleman et al. | |
| 6,592,581 B2 | 7/2003 | Bowe | |
| 6,616,686 B2 | 9/2003 | Wellman et al. | |
| 6,620,161 B2 | 9/2003 | Schulze et al. | |
| 6,623,482 B2 | 9/2003 | Pendekanti et al. | |
| 6,648,900 B2 | 11/2003 | Fleischman et al. | |
| 6,648,901 B2 | 11/2003 | Fleischman et al. | |
| 6,652,521 B2 | 11/2003 | Schulze | |
| 6,656,193 B2 | 12/2003 | Grant et al. | |
| 6,673,084 B1 | 1/2004 | Peterson et al. | |
| 6,685,712 B2 | 2/2004 | Cummins et al. | |
| 6,695,840 B2 | 2/2004 | Schulze et al. | |
| 6,702,828 B2 | 3/2004 | Whayne | |
| 6,767,356 B2 | 7/2004 | Kanner et al. | |
| 6,773,435 B2 | 8/2004 | Schulze et al. | |
| 6,773,439 B2 | 8/2004 | George et al. | |
| 6,773,444 B2 | 8/2004 | Messerly | |
| 6,790,217 B2 | 9/2004 | Schulze et al. | |
| 6,821,273 B2 | 11/2004 | Mollenauer | |
| 6,905,057 B2 | 6/2005 | Swayze et al. | |
| 6,926,731 B2 | 8/2005 | Coleman et al. | |
| 6,939,328 B2 | 9/2005 | Raulerson | |
| 6,951,568 B1 | 10/2005 | Chin | |
| 6,976,969 B2 | 12/2005 | Messerly | |
| 7,041,099 B2 | 5/2006 | Thomas et al. | |
| 7,063,699 B2 | 6/2006 | Hess et al. | |
| 7,090,686 B2 | 8/2006 | Nobles et al. | |
| 7,128,748 B2 | 10/2006 | Mooradian et al. | |
| 7,147,138 B2 | 12/2006 | Shelton, IV | |
| 7,300,444 B1 | 11/2007 | Nielsen et al. | |
| 7,364,060 B2 | 4/2008 | Milliman | |
| 7,396,356 B2 | 7/2008 | Mollenauer | |
| 7,402,172 B2 | 7/2008 | Chin et al. | |
| 7,404,508 B2 | 7/2008 | Smith et al. | |
| 7,419,080 B2 | 9/2008 | Smith et al. | |
| 7,500,979 B2 | 3/2009 | Hueil et al. | |
| 7,556,186 B2 | 7/2009 | Milliman | |
| 7,857,187 B2 | 12/2010 | Milliman | |
| 7,866,523 B1 | 1/2011 | White et al. | |
| 7,963,976 B2 * | 6/2011 | Goldfarb | A61B 17/02 600/141 |
| 8,043,328 B2 * | 10/2011 | Hahnen | A61B 17/07207 606/205 |
| 8,066,166 B2 | 11/2011 | Demmy et al. | |
| 8,123,103 B2 * | 2/2012 | Milliman | A61B 17/068 227/175.1 |
| 8,136,711 B2 * | 3/2012 | Beardsley | A61B 17/07207 227/175.1 |
| 8,403,196 B2 | 3/2013 | Beardsley et al. | |
| 2002/0069884 A1 | 6/2002 | Boyd et al. | |
| 2002/0074004 A1 | 6/2002 | Boyd et al. | |
| 2002/0095175 A1 * | 7/2002 | Brock | A61B 17/0469 606/205 |
| 2002/0173809 A1 | 11/2002 | Fleischman et al. | |
| 2003/0028178 A1 | 2/2003 | Chin | |
| 2003/0144686 A1 | 7/2003 | Martinez et al. | |
| 2004/0068278 A1 | 4/2004 | Fleischman et al. | |
| 2004/0236326 A1 | 11/2004 | Schulze et al. | |
| 2004/0243151 A1 | 12/2004 | Demmy et al. | |
| 2004/0243207 A1 * | 12/2004 | Olson | A61N 1/05 607/116 |
| 2005/0022601 A1 | 2/2005 | Blakley | |
| 2005/0059996 A1 | 3/2005 | Bauman et al. | |
| 2005/0080434 A1 | 4/2005 | Chung et al. | |
| 2005/0096670 A1 | 5/2005 | Wellman et al. | |
| 2005/0096671 A1 | 5/2005 | Wellman et al. | |
| 2005/0119669 A1 | 6/2005 | Demmy | |
| 2005/0131390 A1 * | 6/2005 | Heinrich | A61B 17/0469 606/1 |
| 2005/0143756 A1 | 6/2005 | Jankowski | |
| 2005/0216055 A1 | 9/2005 | Scirica et al. | |
| 2005/0216057 A1 | 9/2005 | Coleman et al. | |
| 2005/0228413 A1 | 10/2005 | Binmoeller et al. | |
| 2005/0228446 A1 | 10/2005 | Mooradian et al. | |
| 2006/0030877 A1 | 2/2006 | Martinez et al. | |
| 2006/0129165 A1 | 6/2006 | Edoga et al. | |
| 2006/0151568 A1 | 7/2006 | Weller et al. | |
| 2006/0200012 A1 * | 9/2006 | Mansour | A61B 5/0059 600/310 |
| 2006/0208028 A1 | 9/2006 | Kanner | |
| 2006/0229643 A1 | 10/2006 | Nolan et al. | |
| 2006/0264986 A1 | 11/2006 | Park et al. | |
| 2007/0005084 A1 | 1/2007 | Clague et al. | |

(56) References Cited

U.S. PATENT DOCUMENTS

| | | | |
|---|---|---|---|
| 2007/0021840 A1 | 1/2007 | Lopera | |
| 2007/0027371 A1* | 2/2007 | Benaron | A61B 5/0031 600/310 |
| 2007/0149993 A1 | 6/2007 | Kasahara et al. | |
| 2007/0187455 A1 | 8/2007 | Demmy et al. | |
| 2007/0221700 A1 | 9/2007 | Ortiz et al. | |
| 2007/0221701 A1 | 9/2007 | Ortiz et al. | |
| 2008/0167644 A1* | 7/2008 | Shelton | A61B 17/07207 606/34 |
| 2008/0249565 A1 | 10/2008 | Michler et al. | |
| 2008/0269793 A1 | 10/2008 | Scirica et al. | |
| 2008/0269801 A1 | 10/2008 | Coleman et al. | |
| 2008/0269802 A1 | 10/2008 | Coleman et al. | |
| 2008/0272173 A1 | 11/2008 | Coleman et al. | |
| 2009/0054908 A1* | 2/2009 | Zand | A61B 5/0071 606/130 |
| 2009/0069806 A1 | 3/2009 | De La Mora Levy et al. | |
| 2009/0234248 A1* | 9/2009 | Zand | A61B 5/0031 600/587 |
| 2010/0094315 A1 | 4/2010 | Beardsley et al. | |
| 2010/0106194 A1* | 4/2010 | Bonutti | A61B 17/0218 606/279 |
| 2011/0101065 A1 | 5/2011 | Milliman | |
| 2011/0226837 A1 | 9/2011 | Baxter, III et al. | |
| 2012/0143218 A1 | 6/2012 | Beardsley et al. | |
| 2012/0298719 A1 | 11/2012 | Shelton, IV et al. | |

FOREIGN PATENT DOCUMENTS

| | | |
|---|---|---|
| EP | 2 263 568 | 12/2010 |
| EP | 2524658 A1 | 11/2012 |
| EP | 2772203 A2 | 9/2014 |
| WO | WO 01/21060 | 3/2001 |
| WO | WO 02/00121 | 1/2002 |
| WO | WO 2004/096057 | 11/2004 |
| WO | WO 2007/147439 | 12/2007 |
| WO | WO 2012/072133 | 6/2012 |
| WO | WO 2013/043674 | 3/2013 |

OTHER PUBLICATIONS

European Search Report for EP 10251721.6-2310 dated Feb. 18, 2011.

European Search Report dated Oct. 24, 2016, issued in European Application No. 16 17 5126.

Chinese Office Action dated Mar. 2, 2017, issued in CN Application No. 201410090929.

Chinese Office Action dated Oct. 17, 2017, issued in CN Appln. No. 201410090929.

European Office Action dated Feb. 12, 2018, issued in EP Appln. No. 16175126.

* cited by examiner

INTERCHANGEABLE TIP RELOAD

CROSS-REFERENCE TO RELATED APPLICATIONS

This application claims the benefit of and priority to U.S. Provisional Patent Application No. 61/777,269, filed Mar. 12, 2013, the entire disclosure of which is incorporated by reference herein.

BACKGROUND

Technical Field

The present disclosure relates generally to a surgical device including an end effector, and more particularly to an end effector configured and adapted to receive and support interchangeable tips to facilitate performing a thoracic surgical procedure.

Background of Related Art

Minimally invasive surgeries are becoming increasingly commonplace due to their advantages, e.g., a faster recovery time and a better cosmetic result. One type of minimally invasive surgical procedure is Video Assisted Thoracic Surgery (VATS) allows doctors to perform chest surgery through small incisions less than an inch long. A camera is inserted through one of the incisions to view the surgical site. The images from the camera are displayed on a video monitor. Other small incisions may be made to receive surgical instruments therethrough.

Numerous devices are used during a thoracic surgical procedure. Such devices include, but not limited to, a thoracoscope, a stapler, a blunt dissector sponge (such as a kittner), a grasper, a dissector, a scissor, and/or a specimen retrieval bag. A continuing need exists to facilitate the use of these varied devices during a minimally invasive surgical procedure while simplifying the procedure and reducing the time to complete the procedure.

SUMMARY

Disclosed herein is a surgical device including an end effector that is configured and adapted to receive an interchangeable tip. Various embodiments of interchangeable tips configured for the performance of different surgical procedures are disclosed herein, and each of the interchangeable tips may be used with the same end effector. In an embodiment, the surgical device includes a handle, an elongated body portion extending from the handle, and the end effector. The end effector includes a cartridge assembly, an anvil assembly, and the interchangeable tip operatively connected to one of the cartridge and anvil assemblies.

The interchangeable tips allow for the performance of an additional procedure or step without necessitating the introduction of another instrument into the surgical site. The interchangeable tips can vary in geometry and material depending on the need. The tips include but are not limited to tips having a sponge material, rubber material, and may also have cautery ability that can be used throughout the procedure. The tip may be a blunt object used to dissect tissue with or without an associated gauze covering, such as a kittner. In embodiments, the interchangeable tip may include a textured surface, a hook, an electrode, and/or a blade.

The interchangeable tip may be operatively coupled to one of the anvil or cartridge assemblies. In embodiments, the interchangeable tip may be magnetically secured to one of the cartridge and anvil assemblies. A magnet on the proximal portion of the interchangeable tip may facilitate proper placement and securing of the interchangeable tip. A carrier may hold one or more interchangeable tips prior to use.

The surgical device described hereinbelow may be used during a surgery such as a minimally invasive surgical procedure, including thoracic surgery. In an embodiment, a surgeon may place an access device between adjacent ribs of a patient to access the patient's thoracic cavity. A plurality of interchangeable tips are provided. A surgeon selects an appropriate interchangeable tip and operably couples the appropriate interchangeable tip with the surgical device. The surgical device is placed within the access device and underlying body structures within the thoracic cavity are operated upon as desired. Once the desired procedure is completed, the surgical device, as well as the access device, is removed.

In another aspect of the present disclosure, a surgical kit is disclosed. The surgical kit includes a surgical device, an end effector assembly, and a carrier. The end effector assembly may be integral to the surgical device. The carrier includes interchangeable tips and a plate having apertures. A proximal end of each tip is secured within an aperture. The carrier may also include a securing member to secure the proximal end of each tip within the aperture. The interchangeable tips are each configured for a different surgical procedure.

These and other aspects of the present disclosure will be described in greater detail when read with reference to the appended figures.

BRIEF DESCRIPTION OF THE DRAWINGS

Embodiments of the present disclosure are described herein with reference to the accompanying figures, wherein:

FIG. 3A is a perspective view of an embodiment of an interchangeable tip;

FIG. 3B is a perspective view of an embodiment of an interchangeable tip;

FIG. 3C is a perspective view of an embodiment of an interchangeable tip;

FIG. 3D a perspective view of a still further embodiment of an interchangeable tip;

DETAILED DESCRIPTION

Figure 1:
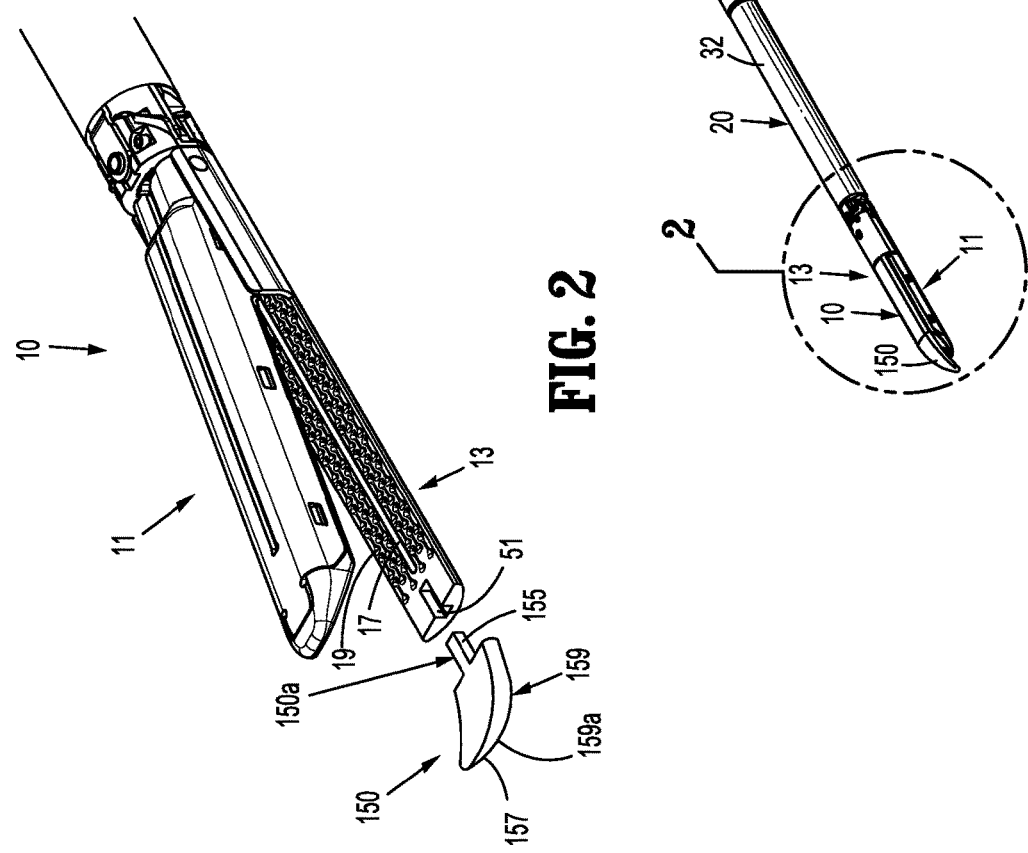
FIG. 1 is a side perspective view of a surgical stapling device including an end effector including an interchangeable tip.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present disclosure.

As used herein, the term "distal," as is conventional, will refer to that portion of the instrument, apparatus, device or component thereof which is farther from the user while, the term "proximal," will refer to that portion of the instrument, apparatus, device or component thereof which is closer to the user. In the following description, well-known functions or constructions are not described in detail to avoid obscuring the present disclosure in unnecessary detail. A surgical device 100 will now be described with reference to FIGS. 1 and 2. The surgical device 100 includes an end effector 10 having an interchangeable tip. The stapling device 100 includes a handle assembly 16 and an elongated body 18. The end effector 10 forms part of a disposable loading unit (DLU) or single use loading unit (SULU) 20. The end effector 10 includes an interchangeable tip 15. Various embodiments of interchangeable tips are disclosed herein. Although the interchangeable tips are described and illustrated as being used in a surgical stapler, such interchangeable tips may be used with other surgical devices including, for example, any linear stapling device of both an endoscopic and open construction and include articulating and non-articulating device, as well as reusable and non-reusable devices.

The handle assembly 16 includes a stationary grip member 22, a pivotable trigger 24, an articulation lever 26, a rotation knob 27, and return knobs 28. SULU 20 is configured and adapted to be releasably attached to the elongated body portion 18. The SULU 20 includes a proximal body portion 32 and the end effector 10. The end effector 10 is pivotally attached to the proximal body portion 32 to facilitate articulation of the end effector 10 in relation to the proximal body portion 32. Examples of surgical stapling devices are shown and described in U.S. Pat. Nos. 5,865, 361; 7,967,178; and U.S. Pat. Pub. No. 2004/0243151, the contents of which are hereby incorporated by reference in their entireties.

Figure 2:
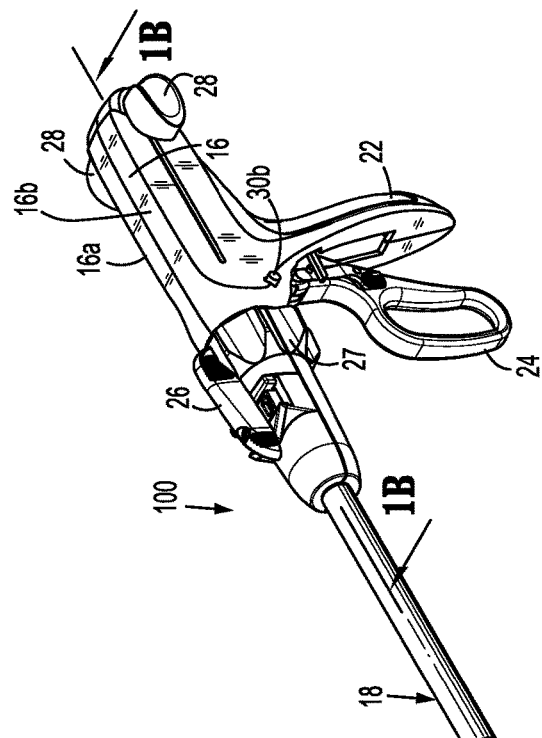
FIG. 2 is an enlarged view of the indicated area of detail shown in FIG. 1.

The end effector 10 will now be described with reference to FIG. 2. As shown in FIG. 2, the end effector 10 includes an anvil assembly 13 and a cartridge assembly 11, which houses surgical fasteners or staples therein. The anvil assembly 13 includes a plurality of concavities 19 to facilitate the formation of completed staples as the anvil assembly 13 and the cartridge assembly 11 are approximated, i.e., in a substantially closed position relative to one another. A channel 17 may extend longitudinally through the anvil assembly 13 to receive a knife blade therethrough.

Anvil assembly 13 and cartridge assembly 11 are movable in a pivotal relation to one another between a substantially open position and a substantially clamped or approximated position. Pivotable trigger 24 (FIG. 1) is actuated through an actuation stroke or strokes to move anvil assembly 13 in relation to cartridge assembly 11 between the open position and the clamped position and to eject staples from the cartridge assembly 11. After the staples have been fired, the trigger 24 may inhibit another firing from occurring. By inhibiting the approximation of the cartridge assembly 11 and the anvil assembly 13 relative to one another after the staples have already been ejected form the cartridge assembly 11, the risk of unintended duct or vessel damage is lessened.

The anvil assembly 13 includes a distal end 150a includes a slot 51 adapted and configured to receive interchangeable tips therein. The particular interchangeable tip inserted into the slot 51 will have particular characteristics that will facilitate the performance of multiple functions by the surgical device 100 that would otherwise necessitate the introduction of another surgical instrument. For example, the interchangeable tips may include, but are not limited to, tips having a sponge, kittner, and/or rubber like materials. In some embodiments, the tips may also function to cauterize tissue.

The clamping and grasping mode of operation of the end effector 10 will now be described with reference to FIGS. 1B-1C. Slide buttons 40, 45 (FIG. 1C) may be configured to alternate the end effector 10 (FIG. 1) between a grasping mode and a firing or clamping mode. The trigger 24 includes a grasping pawl assembly 67 that is operatively associated with slide buttons 40, 45. In the grasping mode, the anvil assembly 13 (FIG. 1) is movable in relation to the cartridge assembly 11 (FIG. 1) between open and approximated positions to grasp tissue therebetween. In the clamping mode, the anvil assembly 13 and the cartridge assembly 11 are movable in relation to each other to grasp tissue therebetween and apply linear rows of staples. In the clamping mode, the refractor knobs 28 (FIG. 1) are used to move the anvil assembly 13 and the cartridge assembly 11 apart, thereby releasing tissue positioned therebetween. Slide buttons 40, 45 each include a raised surface 40a, 45a, respectively. Raised surfaces 40a, 45a are configured to be engaged by a user's finger to move slide buttons 40, 45 within recess 42 (FIG. 1C), respectively. Alternatives to slide buttons 40, 45 may be utilized such as, but not limited to, knobs, levers, depressible buttons, toggles, trigger assemblies, etc.

Actuation of the trigger 24 will be described with reference to FIGS. 1-1C. The trigger 24 is supported between housing half-sections 16a, 16b (FIG. 1) about a cylindrical member (not shown) that is received within an opening 31 within the trigger 24. A biasing member (not shown), e.g., a torsion spring, may be included to urge the trigger 24 away from the grip member 22 to a non-compressed position. As shown in FIG. 1C, the trigger 24 includes a pair of through-bores 33 dimensioned to receive pivot member 34. An advancement pawl 35 is rotatably supported on pivot member 34 and is biased by a spring 36 towards an actuation shaft 90. Actuation member or actuation shaft 90 is slidably supported between retracted and advanced positions, and defines a recess 94 configured to rotatably receive proximal end 97 of a control rod 95. Actuation shaft 90 includes a toothed rack 92. Advancement pawl 35 has an engagement finger 35a which is biased by a spring 36 towards toothed rack 92 of actuation shaft 90. When the trigger 24 is actuated, i.e., is pivoted towards the grip member 22 against the bias of a torsion spring (not shown), engagement finger 35a of pawl 35 engages toothed rack 92 of actuation shaft 90 to advance actuation shaft 90 and the control rod 95 distally.

Actuation member or actuation shaft 90 is slidably supported between refracted and advanced positions within a barrel portion of housing 16 (FIG. 1) and includes a distal end defining a recess 94 configured to rotatably receive the proximal end 97 of a control rod 95. Actuation shaft 90 includes a toothed rack 92. Advancement pawl 35 has an engagement finger 35a which is biased by spring 36 towards toothed rack 92 of actuation shaft 90. When trigger 24 is actuated, i.e., is pivoted towards stationary grip member 22 against the bias of a torsion spring (not shown), engagement finger 35a of pawl 35 engages toothed rack 92 of actuation shaft 90 to advance actuation shaft 90 and control rod 95 distally.

Figure 1B:
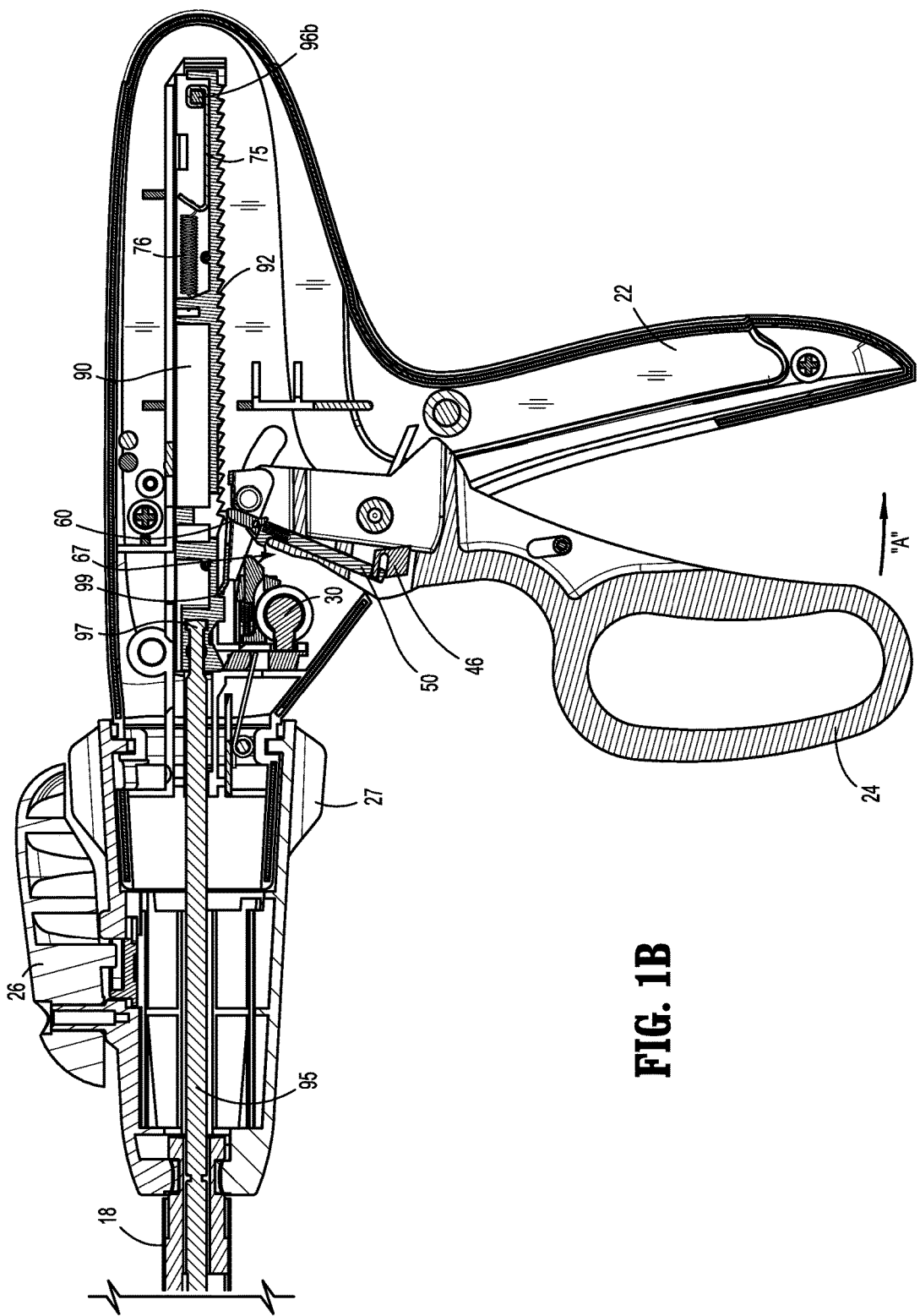
FIG. 1B is a side cross sectional view of surgical stapling device of FIG. 1 taken along section-line 1B-1B.
Figure 1C:
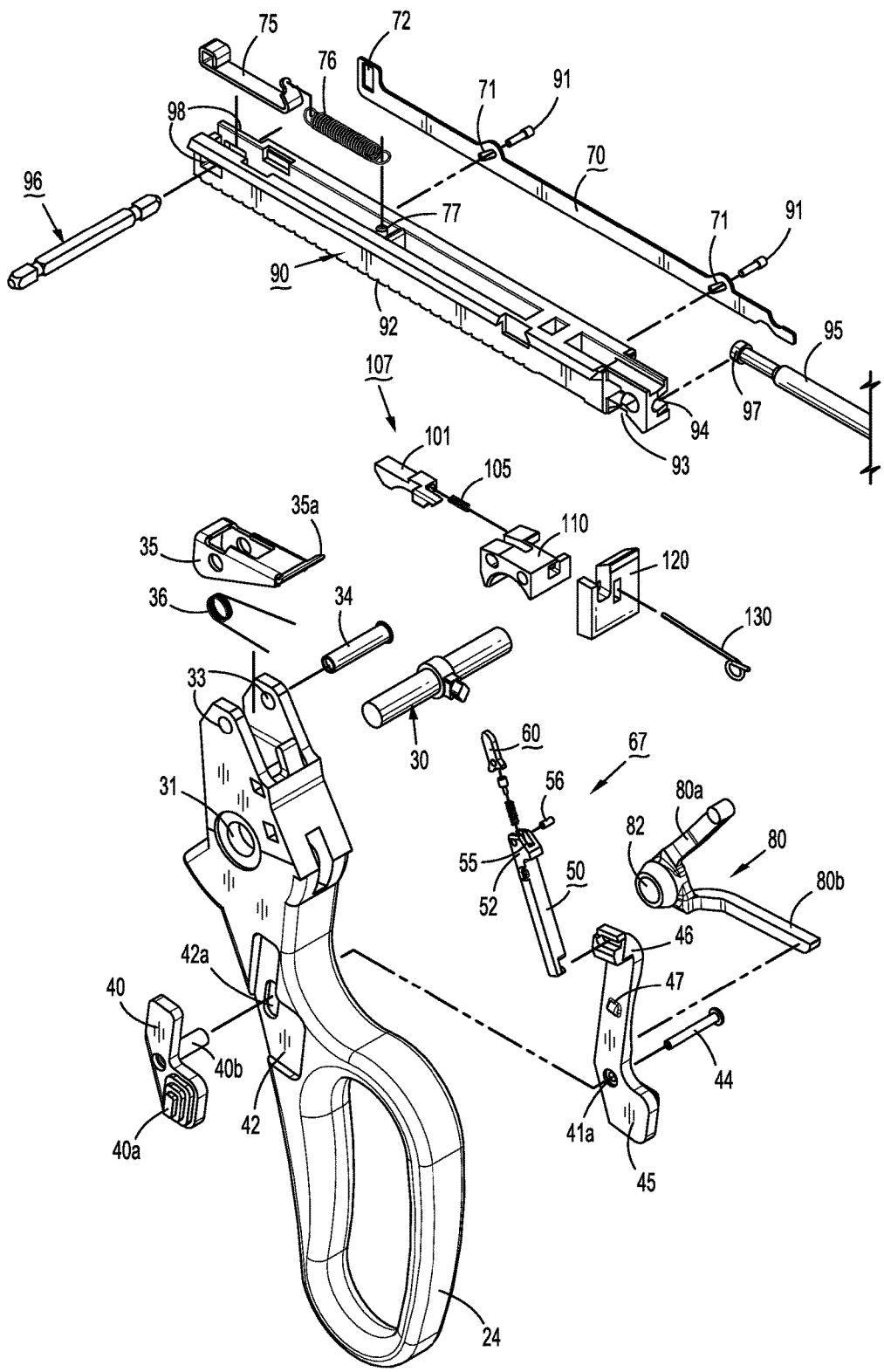
FIG. 1C is a side perspective view of the proximal end of the surgical stapling device shown in FIG. 1 with parts separated.

With continued reference to FIG. 1C, the grasping pawl assembly 67 is operatively associated with slide buttons 40 and 45. Grasping pawl assembly 67 is configured for movement with respect thereto in response to manipulation of slide buttons 40 and 45. Grasping pawl assembly 67 includes a slider or other engagement member such as pawl arm 50 and grasping pawl 60. Pawl arm 50 has a sloped surface 55 defined on an outturned portion 52 of a top end of pawl arm 50, and grasping pawl 60 is pivotally supported within outturned portion 52 of pawl arm 50. A top end of slide button 45 includes an in-turned portion 46 having an extension that defines a recessed groove. The recessed groove is dimensioned and configured to slidably receive an extension defined by a recessed groove in a bottom end of pawl arm 50. Reciprocally, the recessed groove in pawl arm 50 is dimensioned and configured for slidably receiving an extension of slide button 45. A bottom end of slide button 45 includes an opening 41 a configured to receive a connector pin 44 therethrough. A cylindrical receptacle 40b extends outwardly from an inner surface of slide button 40 and is configured and dimensioned to translate within a longitudinal slot 42a formed in recess 42 of trigger 24. Connector pin 44 is dimensioned to be received within receptacle 40b to secure slide button 45 to slide button 40.

Referring to FIGS. 1B-1C, movement of the trigger 24 in the direction of arrow "A" (FIG. 1B) through a grasping stroke moves engagement finger 35a of advancement pawl 35 into engagement with a shoulder 99 formed on actuation shaft 90. Subsequent movement of trigger 24 through the grasping stroke rotates pawl arm 50 counter-clockwise. As trigger 24 returns to its initial position, arm 80b of yoke 80 slides slide buttons 40, 45 upwardly, so that the surgical device 100 remains in grasping mode. Sliding slide buttons 40, 45 downwardly causes subsequent movement of trigger 24 in the direction "A" clamps cartridge assembly 11 and anvil assembly 13 onto tissue. Yoke 80 is rotatably supported within the stationary grip member 22 about a cylindrical member (not shown) which is received within an opening 82 within yoke 80. A pair of arms 80a and 80b extend laterally from opening 82. Upon movement of the trigger 24 in the direction indicated by arrow "A", i.e., pivoted towards stationary grip member 22, slide buttons 40 and 45 are movable from an upward position in which grasping pawl 60 is engaged in a slot 92b in toothed rack 92 of actuation shaft 90, to a downward position in which grasping pawl 60 is spaced from toothed rack 92 of actuation shaft 90. When grasping pawl 60 is positioned within slot 92b, only limited advancement and retraction of the actuation shaft 90 will occur upon operation of trigger 24, allowing the surgical device 100 to operate in the grasping mode. Sliding slide buttons 40, 45 down moves grasping pawl 60 away from slot 92b and pawl arm 50 away from cam member 101 of locking cam assembly 107. The locking cam assembly 107 includes cam member 101 that is movable between a retracted and extended position to operatively interact vertical pawl 120. The cam member 101 is biased proximally by a spring 105 that engages a spring support 110 that is positioned between cam member 101 and the vertical pawl 120. A spring 130 supported between housing half-sections 16a and 16b is positioned to bias vertical pawl 120 to the extended position. In the extended position, vertical pawl 120 prevents advancement of actuation shaft 90 to prevent firing of the surgical device 100. When the vertical pawl 120 is in the extended position, advancement of actuation shaft 90 is inhibited to inhibit firing of the surgical device 100.

As seen in FIG. 1C, when retractor knobs 28 are pulled rearwardly or proximally, coupling rod 96 initially moves release plate 70 rearward in relation to actuation shaft 90 as coupling rod 96 slides in slots 98 of actuation shaft 90. As this occurs, release plate 70 is moved downwardly by pins 91 with respect to actuation shaft 90 thereby covering toothed rack 92 to disengage engaging finger 35a of advancement pawl 35 from toothed rack 92. The release plate 70 is supported on one side of actuation shaft 90 by a pair of spaced apart pins 91. Pins 91 extend outwardly from a lateral face of actuation shaft 90 to engage a pair of angled cam slots 71 formed through release plate 70. In this way, release plate 70 is operatively associated with actuation shaft 90 and is mounted for movement with respect thereto in response to manipulation of retractor knobs 28. Once coupling rod 96 reaches a position at which it engages the proximal end of slots 98, additional rearward movement of retractor knobs 28 causes retraction of actuation shaft 90 and thus refraction of control rod 95 rearwardly. Actuation shaft 90 is biased proximally by spring 76 which is secured at one end to coupling rod portion 96c via a connector 75 and at the other end to a post 77 on actuation shaft 90.

When the trigger 24 is manipulated to clamp tissue, grasping pawl 60 moves into slot 92 such that vertical pawl 120 engages cutout 93. Plunger 30 is pushed and releases vertical pawl 120. When trigger 24 is manipulated, advancement pawl 35 advances toothed rack 92, and results in the firing of staples. Multiple strokes of trigger 24 are used to advance toothed rack 92, with advancement pawl 35 repeatedly engaging and disengaging toothed rack 92. Yoke 80 maintains slide buttons 40, 45 in the upward position during firing. After retractor knobs 28 are used to retract toothed rack 92, grasping pawl 60 is aligned with slot 92b and the surgical device 100 is in the grasping mode again.

Exemplary embodiments of interchangeable tips that are each operatively connectable to one of the anvil or cartridge assemblies are shown in FIG. 2 and FIGS. 3A-3E. Each interchangeable tip 150, 195, 135, 125, 146, and 400 includes a proximal end 155 that is releasably securable within the slot 51 of the anvil assembly 13. The proximal end 155 may be frictionally secured within the slot 51 of the anvil assembly 13. In an embodiment, the proximal end 155 and the distal end 150a of the anvil 13 may alternatively, or additionally, be formed from materials that will magnetically attract one another to facilitate magnetic securing of the proximal end 155 and the anvil 13. The magnetic attraction of the proximal end 155 and the proximal end 50 may facilitate proper alignment and a relatively easy placement of the interchangeable tip on the distal end 150a of the anvil. In embodiments, adhesive materials may also be used. It is also envisioned that the proximal end 155 and the anvil 13 may include a snap-fit configuration.

As shown in FIG. 2, the interchangeable tip 150 includes proximal end 150 and a distal portion 159. The distal portion 159 may be formed from or coated with a luminescent or fluorescent material and/or coating to facilitate viewing and location of the end effector 10 within a surgical site. The luminescent or fluorescent material and/or coating may facilitate identification of particular tips in the surgical field or behind tissue. Such a coating and/or material may be incorporated into any of the interchangeable tips described herein. A number of other coatings are also envisioned, such as biocompatible material. The distal portion 159 includes a distal end 157 that is upwardly directed to facilitate proper placement of tissue between the anvil assembly 13 and the cartridge assembly 11, e.g., tissue placed between the anvil assembly 13 and the cartridge assembly 11 is directed toward the cartridge assembly 11. A surface 159a of the distal portion 159 of the interchangeable tip 150 may be relatively blunt to facilitate manipulation of tissue, e.g., dividing tissue planes, without cutting or damaging tissue. The distal end 157, however, may be substantially sharp or pointed to facilitate cutting and/or scraping of tissue. The distal end 157 may include a substantially sharp portion and a substantially blunt portion.

Figure 3E:
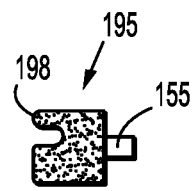
FIG. 3E is a perspective view of an embodiment of an interchangeable tip.
Figure 3E:
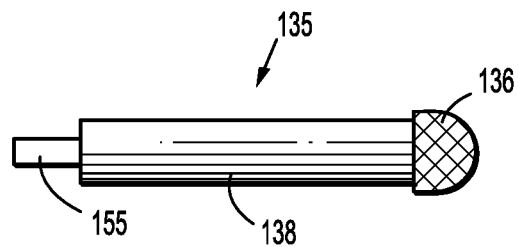
Figure 3E:
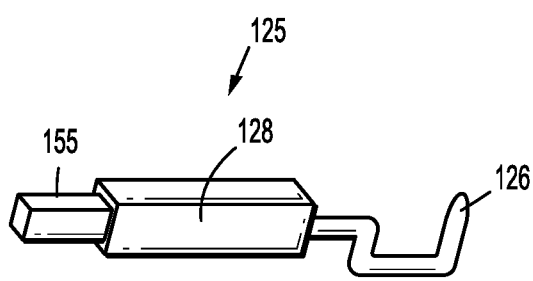
Figure 3E:
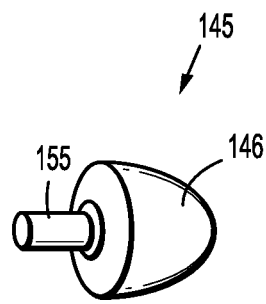
Figure 3E:
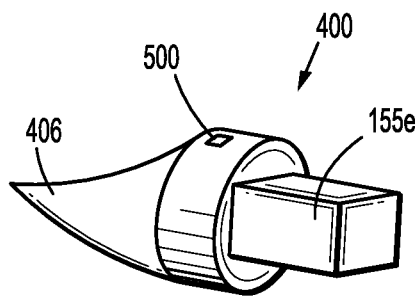

Other embodiments of interchangeable tips will now be described will reference to FIGS. 3A-3E. As shown in FIG. 3A, interchangeable tip 195 includes the proximal end 155 for the placement of the interchangeable tip 195 in a releasably secured relationship with the distal end 150a of the anvil 13 (FIG. 1). The interchangeable tip 195 includes a textured or roughened surface to facilitate gripping of tissue. Various protrusions such as ridges 198 may also facilitate gripping and manipulation of tissue that comes into contact with the interchangeable tip 195. During use, the ridges 198 may facilitate scraping of tissue if desired.

The presence of bodily fluids, e.g., blood, may increase the difficulty of viewing a surgical site and may also present other issues to the patient. It may therefore be desirable to use a kittner tip (a gauze covering or similarly absorbent material covering acting as a sponge for blood and other bodily fluids that may be attached to or used in association with a blunt dissection tip) to absorb the bodily fluids that may be present at the surgical site. As shown in FIG. 3B, an interchangeable tip 135 is configured and adapted to function as a kittner to absorb minor but bothersome bleeding. The interchangeable tip 135 includes the proximal end 155 for the placement of the interchangeable tip at the distal end 150a of the anvil assembly 13 (FIG. 1). The interchangeable tip 135 may include an elongated segment 138 and a distal end 136 formed from a gauze like material. The elongated segment 138 and the distal end 136 may be substantially the same thickness as the distal end 150a of the anvil assembly 13.

In an embodiment, as shown in FIG. 3C, interchangeable tip 125 includes the proximal end 155 for releasably securing the interchangeable tip to the distal end 150a of the anvil assembly 13 (FIG. 1). The interchangeable tip may include an elongated section 128 and a hook 126 to facilitate manipulation, e.g., picking, piercing, and/or scraping, of tissue. As shown in FIG. 3D, an interchangeable tip 145 includes a proximal portion 155 that is releasably secured within slot 51 of the anvil assembly 13. The interchangeable tip, such as tip 145, may includes a portion, such as head 146, that may be formed from an impact-absorbent or rubber-like material. The head 146 functions as a cushion to lessen impact that may occur between the end effector 10 and tissue, thereby minimizing the risk of injury.

The interchangeable tips described herein may include electrodes that are operatively coupled to a generator (not shown) to facilitate cauterization of tissue, thereby reducing potential bleeding of tissue. Electrodes may also be used to cauterize, cut, coagulate, or seal. In an embodiment, as show in FIG. 3E, an interchangeable tip 400 includes a proximal end 155e that is releasably securable within slot 51 (FIG. 2) of the anvil assembly 13. The proximal end 155e is substantially similar to the proximal end 155, except that it is electrically connectable to a power source or a generator (not shown) to send electrical energy, e.g., RF energy, to an electrical blade 406. In embodiments, the proximal end 155e electrically connects to the power source or generator through a cable (not shown) that extends through a portion of the elongate body. A return electrode (not shown) may be placed elsewhere on the patient. The electrical blade 406 may have a different configuration depending upon the desired procedure and may be used for a variety of procedures such as cauterization, cutting, coagulation, and/or sealing of tissue.

The interchangeable tip may also include at least one sensor 500 (FIG. 3E), such as a camera. It is also envisioned that the interchangeable tip may include any combination of the configurations disclosed herein.

Figure 4A:
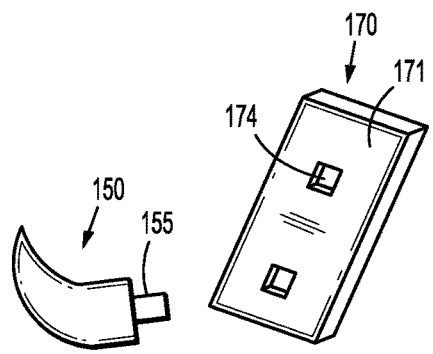
FIG. 4A is a perspective view of an embodiment of a carrier shown relative to the interchangeable tip of FIG. 2.
Figure 4B:
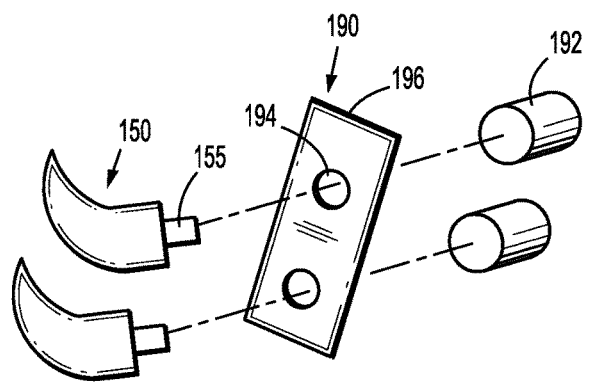
FIG. 4B is a perspective view of another embodiment of a carrier shown relative to the interchangeable tip of FIG. 2.
Figure 4C:
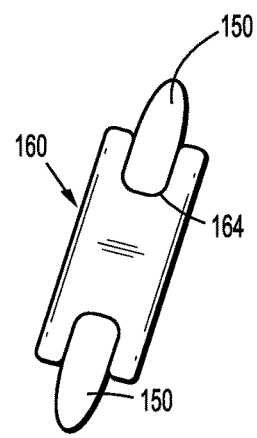
FIG. 4C is a perspective view of an embodiment of a carrier shown with the interchangeable tip of FIG. 2.

One or more interchangeable tips (e.g., interchangeable tip 195, 135, 125, 145, 400) may be stored prior to use in a carrier. Embodiments of carriers will now be described with respect to FIGS. 4A-4C. As shown in FIG. 4A, a carrier 170 includes a plate 171, which includes one or more receptacles 174 for the releasable securing of interchangeable tips, e.g., interchangeable tip 150. The receptacles 174 and the proximal ends of the interchangeable tips, e.g., proximal ends 155 of interchangeable tips 150, are magnetically and/or frictionally secured within the receptacles 174. In an embodiment, as shown in FIG. 4B, a carrier 190 includes a plate 196 and one or more apertures 194 configured and adapted to receive the proximal ends of the interchangeable tips, e.g., proximal ends 155 of interchangeable tips 150. A securing member 192 positioned on an opposing side of the plate 196 operatively couples the interchangeable tip to the plate 196. In embodiments, the securing member 192 magnetically couples the interchangeable tip to the plate 196. In some embodiments, as shown in FIG. 4C, a carrier 160 includes one or more recesses 164 that are configured and adapted to frictionally secure an interchangeable tip, e.g., interchangeable tip 150, therein.

Figure 5:
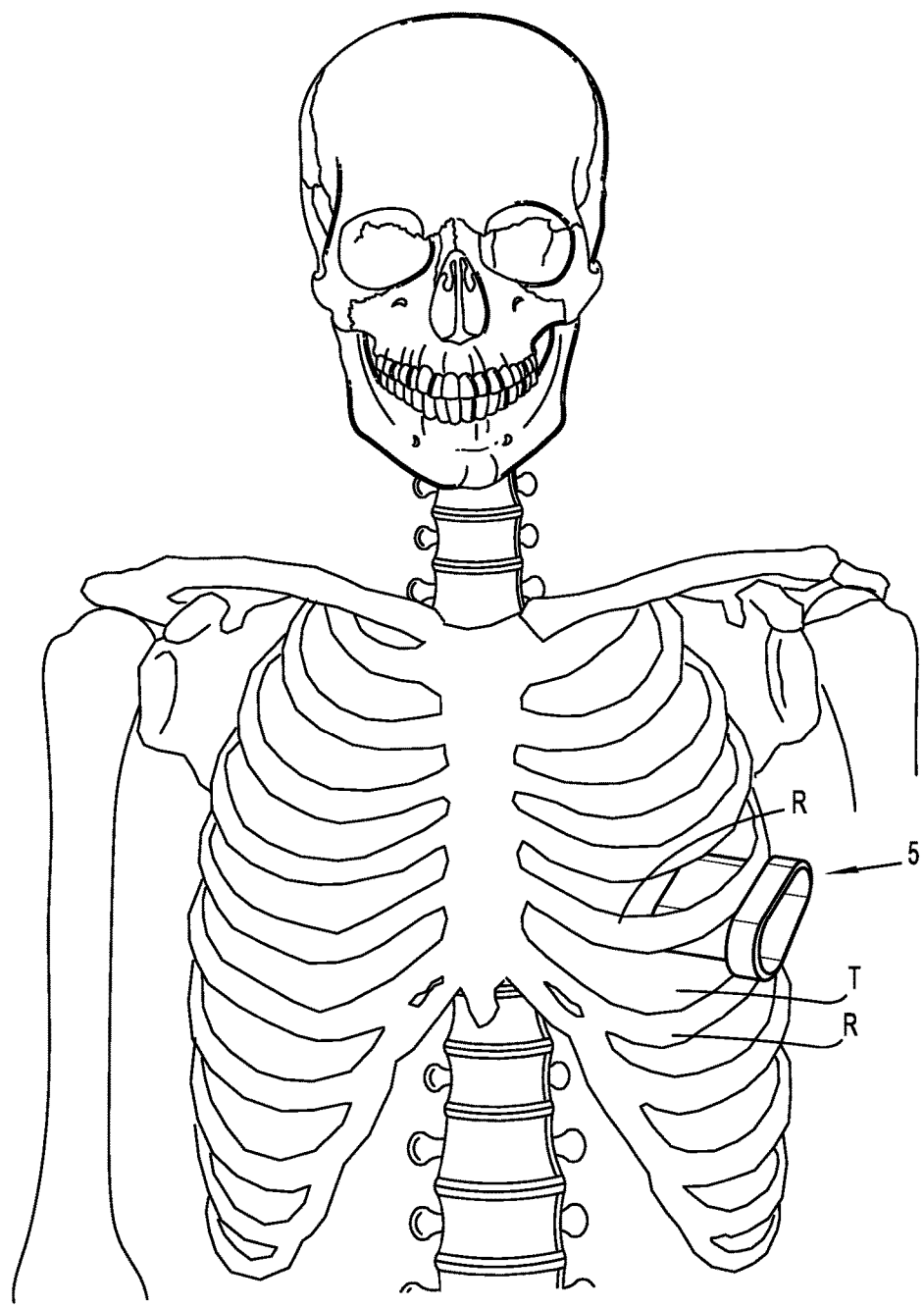
FIG. 5 is a front view illustrating a patient's skeletal structure with an embodiment of the presently disclosed surgical access assembly positioned within the intercostal space defined between adjacent ribs in accordance with the present disclosure.

As shown in FIG. 5, an access assembly 5 may be used to facilitate insertion and manipulation of one or more surgical instruments, e.g., surgical device 100 (FIG. 2), within the thoracic cavity "T". The access assembly 5 is configured and dimensioned to be inserted into the intercostal space located between the adjacent ribs "R" of patient "P" through an opening, e.g., an incision, in the patient's skin. It should be understood that the access assembly 5 may be placed within any suitable body opening, whether naturally occurring (e.g., mouth, anus, and/or vagina) or within an incision, and is not limited to placement between ribs "R" to access the thoracic cavity "T". It should be understood that the access assembly 5 may be formed from any suitable biocompatible material, e.g., polymeric materials.

The surgical device 100 described above is insertable into the access assembly 5 (FIG. 5) to access underlying body structures within the thoracic cavity "T". During use, a surgeon selects an appropriate interchangeable tip (e.g., interchangeable tip 195, 135, 125, 145, 400) depending upon the desired procedure, and operatively couples that interchangeable tip to the distal end 150a of the anvil 13 (FIG. 1). As discussed above, the interchangeable tip is releasably secured to the anvil 13 by means that may include frictional and/or magnetic means. As discussed above, prior to use, the interchangeable tips may be stored in a carrier. By facilitating the performance of multiple surgical procedures by using a single device, the performance of surgical procedures is easier and faster.

Although shown and described for use during a thoracic surgical procedure, e.g., pulmonary artery ligation in the thoracic cavity, the devices and methods described herein have broad surgical applications including endoscopic and open abdominal, gynecologic, and thoracic, breast, and vascular surgery including vessel ligation and tissue removal.

According to another aspect of the present disclosure, a surgical kit is disclosed. The surgical kit includes a surgical device, an end effector assembly, and a carrier. The end effector assembly may be integral to the surgical device. The carrier includes interchangeable tips and a plate having apertures. A proximal end of each tip is secured within an aperture. The carrier may also include a securing member to secure the proximal end of each tip within the aperture. The interchangeable tips are each configured for a different surgical procedure. Any of the surgical devices, DLUs, SULUs, interchangeable tips, and carriers disclosed herein may be included in the surgical kit.

Each of the embodiments described above are provided for illustrative purposes only. It will be understood that various modifications may be made to the embodiments of the present disclosure. Therefore, the above description should not be construed as limiting, but merely as exemplifications of embodiments. Those skilled in the art will envision other modifications within the scope and spirit of the present disclosure.

What is claimed is:

1. A surgical device comprising:
   a handle;
   an elongated body portion extending distally from the handle; and
   an end effector including:
      a cartridge assembly including a plurality of staples;
      an anvil assembly, the cartridge assembly and the anvil assembly movable relative to one another; and
      an interchangeable tip releasably securable to at least one of the cartridge or anvil assemblies to extend distally from the at least one of the cartridge or anvil assemblies, the interchangeable tip including a sensor.

2. The surgical device of claim 1, wherein the end effector includes a first jaw, the cartridge assembly releasably received within the first jaw.

* * * * *